United States Patent [19]

Hoffman et al.

[11] Patent Number: 5,000,744
[45] Date of Patent: Mar. 19, 1991

[54] HYPODERMIC SYRINGE

[75] Inventors: J. Kenneth Hoffman, Warren, Pa.; Joseph W. Blake, III, New Canaan, Conn.

[73] Assignee: GTE Products Corporation, Stamford, Conn.

[21] Appl. No.: 542,503

[22] Filed: Jun. 25, 1990

Related U.S. Application Data

[62] Division of Ser. No. 425,253, Oct. 23, 1989.

[51] Int. Cl.$^5$ .............................................. A61M 5/00
[52] U.S. Cl. ................................................... 604/232
[58] Field of Search .................. 604/232, 187, 198

[56] References Cited

U.S. PATENT DOCUMENTS

| | | | |
|---|---|---|---|
| 3,115,135 | 12/1963 | Sarnoff | 604/232 |
| 4,915,701 | 4/1990 | Halkyard | 604/232 X |
| 4,935,016 | 6/1990 | Deleo | 604/198 |

FOREIGN PATENT DOCUMENTS 562017 4/1958 Belgium ............................. 604/232

Primary Examiner—John D. Yasko
Attorney, Agent, or Firm—William H. McNeill

[57] ABSTRACT

An inner elongated tubular member having a plurality of arms which extend from one end thereof and a concentric outer sleeve slideable relative to the tubular member for urging each of the arms into engagement with the hub of a needle attached to one end of a medicament cartridge to lock the cartridge and its needle to the tubular member and form a hypodermic needle.

6 Claims, 3 Drawing Sheets

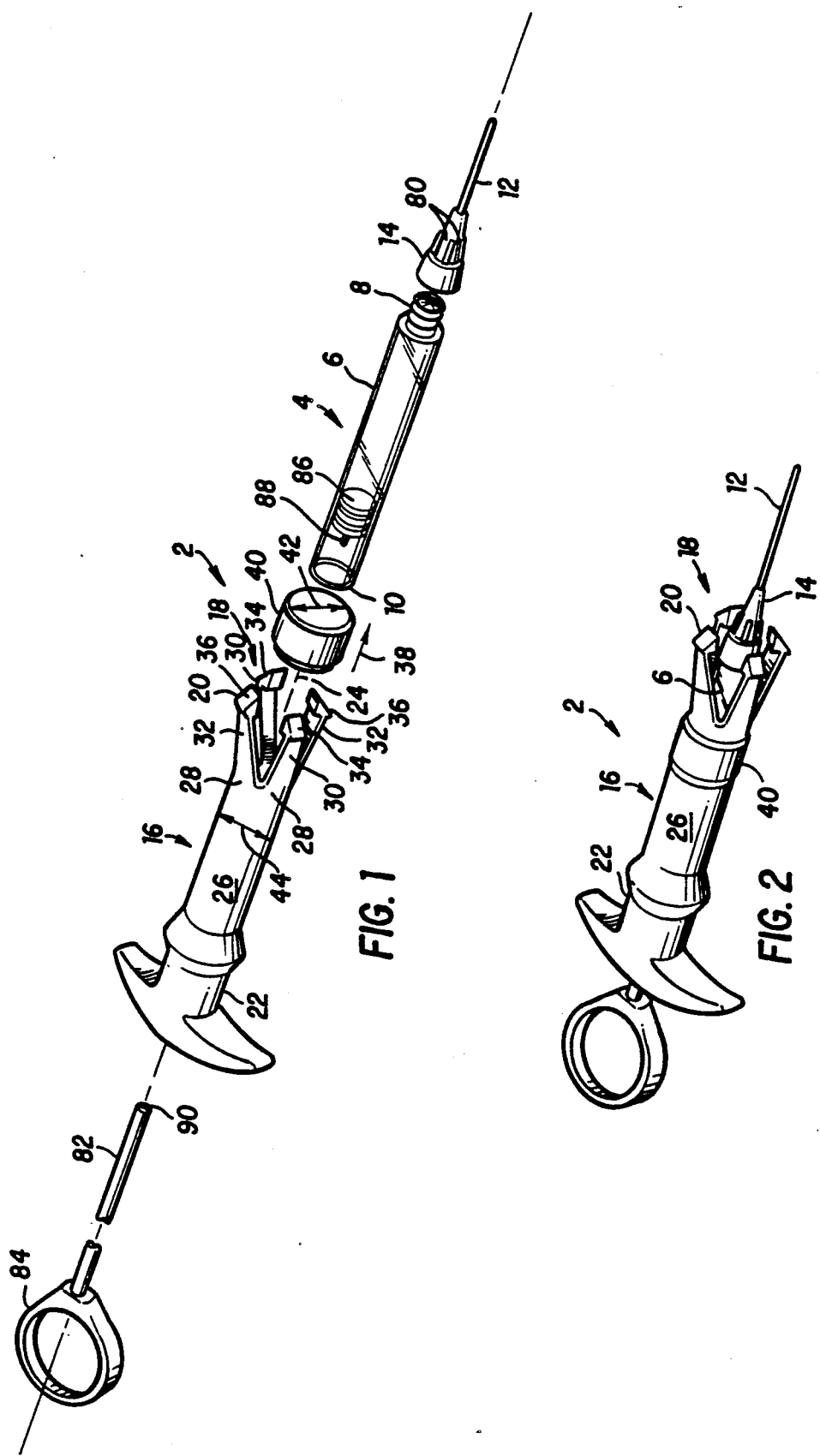

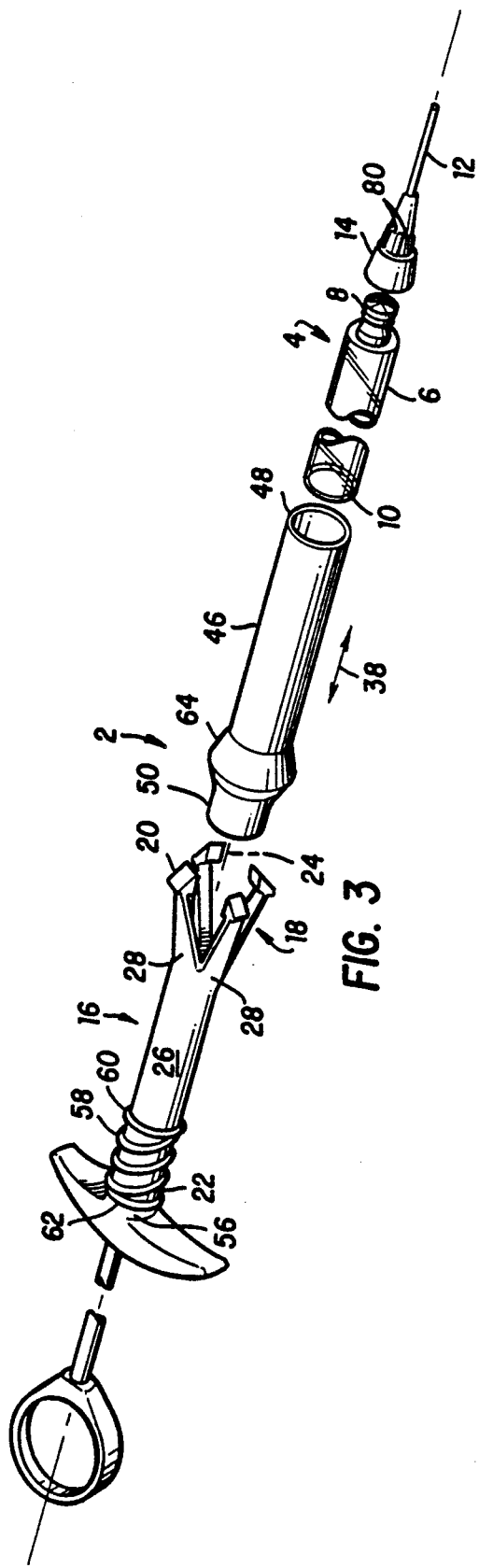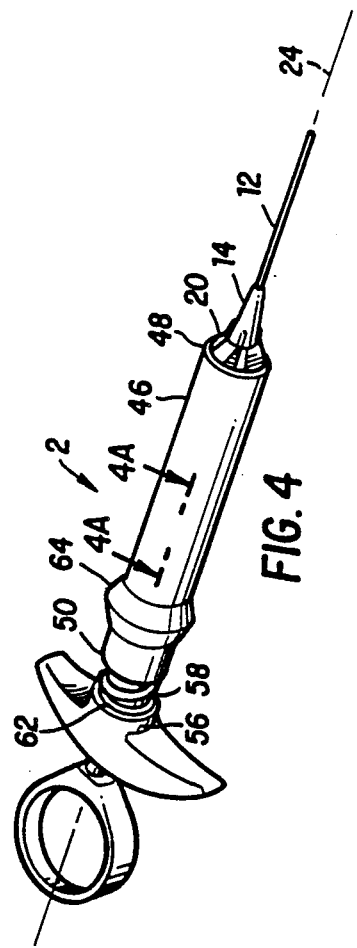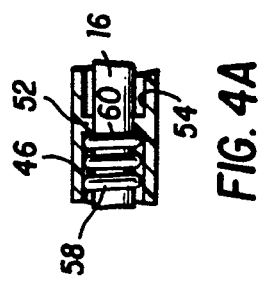

HYPODERMIC SYRINGE

This is a division of copending application Ser. No. 07/425,253, filed on Oct. 23, 1989.

BACKGROUND OF THE INVENTION

1. Field of the Invention

The present invention relates to a device for holding a cartridge having a needle attached thereto and for dispensing medicament from the cartridge or drawing blood into the cartridge. When coupled together, the holding device, cartridge and needle form a hypodermic syringe.

2. Description of the Prior Art

One form of hypodermic syringe typically includes a generally cylindrical barrel including a piston rod therein. The rod includes a handle at one end to facilitate reciprocating movement of the rod within the cylindrical barrel. In such a hypodermic syringe a cartridge is provided having a needle attached thereto, the cartridge being inserted into the cylindrical barrel to work in combination with the piston rod to dispense or receive liquid such as medicament or blood, respectively, in response to movement of the piston rod within the barrel. In this form of syringe the piston rod is connected to a plunger in the inserted cartridge, axial movement of the piston rod causing corresponding axial movement of the plunger to dispense the medicament from the cartridge or receive blood within the cartridge depending upon whether such movement is a dispensing movement or aspirating movement. Such hypodermic needles are well known in the art and examples include embodiments described in U.S. Pat. Nos. 2,524,367 to Smith and 4,744,790 to Jankowski et al.

One problem that occurs during use of such a hypodermic syringe is that of accidental exposure of the user of the syringe to whatever contaminants might be present upon or within the needle or cartridge after use thereof. For example, in those instances where the needle and cartridge are to be removed from the barrel and disposed of, heretofore it has been necessary for the user to grasp the needle to remove the needle and cartridge assembly from the barrel. Such grasping can expose the attendant to any contaminant which is on the exterior surface of the needle and cartridge, particularly if the attendant is not wearing a glove. In addition, not infrequently the attendant might be accidentally punctured by the needle while attempting to remove the needle and cartridge and corresponding contamination of the user will obviously result. Somewhat related to these problems is the not unlikely possibility that the attendant might drop the needle and cartridge assembly while removing the assembly from the barrel structure resulting in undersirable contamination of the area exposed to the needle and cartridge. A similar problem is the possibility that the needle and cartridge assembly might prematurely fall out of the barrel-like holder during the disposal operation. In any event, accidental contamination of a medical attendant or anyone else can present a serious health problem especially if the contaminant is an infectious disease such as hepatitis, AIDS and the like.

In order to prevent undesirable contamination, it is highly desirable to provide a hypodermic syringe wherein a medical attendant can remove a cartridge and needle assembly from an associated holder without grasping or otherwise touching the assembly. Similarly, it is also desirable to provide a hypodermic syringe wherein a medical attendant can remove such an assembly without the assembly prematurely falling out of the holder as a result of the attendant carelessly attempting to grasp the assembly and without the attendant inadvertently dropping the assembly.

SUMMARY OF THE INVENTION

This invention achieves these and other results by providing apparatus for use with a cartridge to form a hypodermic syringe. The cartridge includes an elongated body having a first end and a second end and having a needle attached to the first end by means of a hub which is attached to one end of the needle. The device comprises an elongated tubular member having one end which includes a plurality of arms extending therefrom and an opposite other end. The arms are moveable in a radial direction relative to a longitudinal axis of the elongated tubular member and are resiliently biased away from the longitudinal axis. The elongated tubular member is configured such that the cartridge is insertable into the elongated tubular member at the second end of the cartridge until the hub is adjacent the plurality of arms and the needle is extending from the elongated tubular member in the direction of the longitudinal axis. Means is positioned around the elongated tubular member and is slideable relative to the elongated tubular member in the direction of the longitudinal axis, for urging each arm of the plurality of arms towards the longitudinal axis, and into locking engagement with the hub when the cartridge has been inserted into the elongated tubular member, as the means is moved towards the one end and engages the plurality of arms. Means is associated with the elongated tubular member for dispensing and aspirating the hypodermic syringe which is formed when the cartridge is inserted into and coupled to the elongated tubular member.

BRIEF DESCRIPTION OF THE DRAWINGS

FIG. 1 is an exploded perspective view of one embodiment of the present invention;

FIG. 2 is an assembled perspective view of the embodiment of FIG. 1 in an open or unlocked position;

FIG. 3 is an exploded perspective view of another embodiment of the present view;

FIG. 4 is an assembled perspective view of the embodiment of FIG. 3 in a closed or locked position;

FIG. 4A is a sectional view taken along 4A—4A of FIG. 4;

DESCRIPTION OF THE PREFERRED EMBODIMENT

Figures 5, 6:
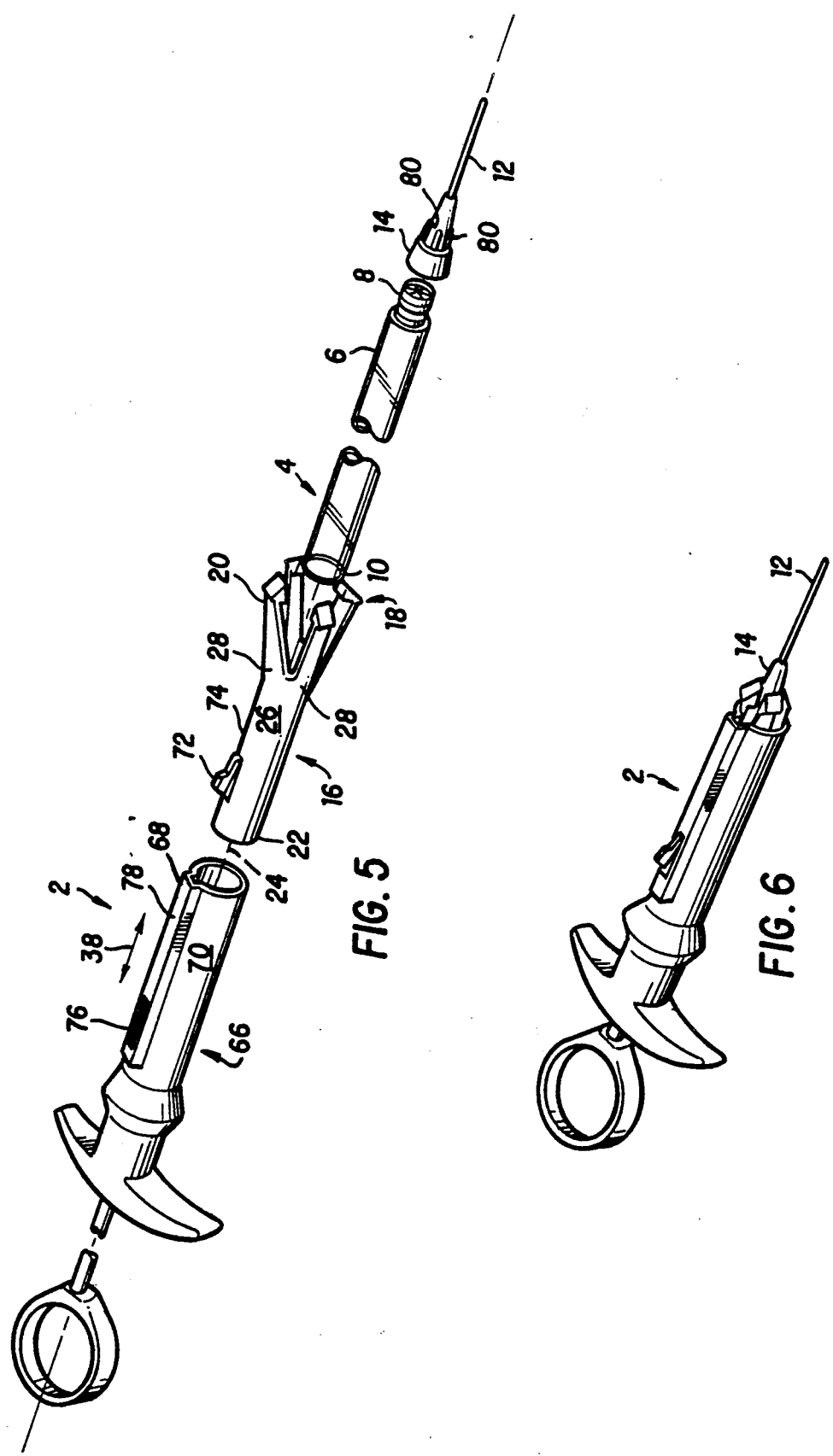
FIG. 5 is an exploded perspective view of yet another embodiment of the present invention.
FIG. 6 is an assembled perspective view of the embodiment of FIG. 5 in a closed or locked position.

The embodiments of this invention which are illustrated in FIGS. 1 to 6 are particularly suited for achieving the objects of this invention. FIGS. 1 to 6 depict apparatus for use with a cartridge to form a hypodermic syringe 2. The cartridge 4 includes an elongated body 6 which is preferably glass. Body 6 includes a first end 8, a second end 10 and a needle 12 which is attached to first end 8 by means of a hub 14 which is attached to one end of the needle in a known manner.

An elongated tubular member 16 is also provided having one end 18 which includes a plurality of arms 20 extending therefrom and an opposite other end 22. The elongated tubular member 16 is preferably polycarbonate. The individual arms which comprise the plurality of arms 20 are moveable in a radial direction relative to a longitudinal axis 24 of the elongated tubular member 16 and are resiliently biased away from longitudinal axis 24 as depicted in FIGS. 1, 3 and 5. The elongated tubular member 16 is configured such that the cartridge 6 can be inserted into member 16 at second end 10 of the cartridge, the cartridge being inserted to the point where the hub 14 is adjacent the plurality of arms 20 and the needle 12 extends from the member 16 in the direction of the longitudinal axis 24, as depicted in FIGS. 2, 4 and 6.

In the preferred embodiment the elongated tubular member 16 and the plurality of arms 20 are formed by a unitary structure. In such structure, the member 16 includes a body portion 26, and each of the plurality of arms 20 is integrally hinged to the body portion 26 and extends at an angle away from the body portion at a respective hinge 28, as depicted in FIGS. 1, 3 and 5. In the preferred embodiment, the plurality of arms 20 comprises two pairs of opposing arms, such as, for example, the first pair of opposing arms 30 and the second pair of opposing arms 32 depicted in FIG. 1. In the embodiment depicted in the drawings the plurality of arms 20 comprise two pairs of opposing claw-like arms. For example, as depicted in FIG. 1, opposing arms 30 include claw-like ends 34 and opposing arms 32 include claw-like ends 36. Preferably, each arm of the plurality of arms 20 is circumferentially spaced at about ninety degrees from an adjacent arm, as depicted in FIGS. 1, 3 and 5.

Means is positioned around the elongated tubular member 16 and is slideable relative to member 16 in the direction of longitudinal axis 24 for urging each arm of the plurality of arms 20 radially towards axis 24 as such means is moved towards end 18 and engages the plurality of arms. In this manner the arms of the plurality of arms 20 will be urged into locking engagement with the hub 14 in those instances when the cartridge has been inserted into the elongated tubular member 16 and such means has been moved in the direction of the arrow 38. In the preferred embodiment, a body portion 26 is provided which is cylindrical and an urging means is provided in the form of a polypropylene sleeve having an inner diameter which is greater than an outer diameter of the body portion. Such a configuration facilitates sliding movement of the sleeve relative to the body portion along longitudinal axis 24. For example, in the embodiment depicted in FIGS. 1 and 2, body portion 26 is cylindrical and the urging means is a sleeve 40 having an inner diameter 42 which is greater than outer diameter 44 of body portion 26 to facilitate sliding of the sleeve 40 relative to the body portion 26. In the embodiment of FIGS. 1 and 2 the length of sleeve 40 is less than the length of the body portion 26 measured in the direction of the axis 24.

Referring to FIG. 2, it will be readily apparent that by sliding sleeve 40 towards end 18 of the elongated tubular member 16 the inner surface of sleeve 40 will engage the arms of the plurality of arm 20 and by virtue of a camming action urge the arms radially towards the axis 24 into locking engagement with hub 14 to thereby lock the hub and its needle in place vis-a-vis the elongated tubular member to form the hypodermic syringe 2. The subsequent sliding of sleeve 40 in the opposite direction towards end 22 will allow the arms to move radially away form axis 24 and disengage the hub 14 due to the resiliency and original angular orientation of the arms. In this manner the cartridge can be removed from the elongated tubular member without the attendant touching the cartridge or needle.

In the alternative embodiment of FIGS. 3, 4 and 4A, an elongated sleeve 46 is provided. Sleeve 46 is preferably polypropylene. Sleeve 46 includes an end 48 adjacent the plurality of arms 20 and an opposite end 50. Referring to FIG. 4A, the sleeve further includes a first rest 52 which extends from an inner surface 54 of the sleeve 46. The elongated tubular member 16 in FIGS. 3, 4, and 4A is preferably polypropylene and includes a second rest 56 at end 22 of member 16. A stainless steel compression spring 58 is provided, spring 58 being externally concentric with elongated tubular member 16 and internally concentric with sleeve 46 as depicted in FIG. 4A. A first end 60 of spring 58 bears against the first rest 52 and a second end 62 of the spring bears against the second rest 56. Means is provided for facilitating sliding movement of the sleeve 46 relative to the elongated tubular member 16 in the direction of longitudinal axis 24. For example, in the embodiment depicted in FIGS. 3 and 4, an outwardly expanding section 64 of the sleeve 46 is provided.

In the operation of the embodiment of FIGS. 3, 4 and 4A, the sleeve 46 can be grasped at the section 64 and caused to move in the direction of longitudinal axis 24 towards rest 56 by compressing spring 58 between rests 52 and 56. Such movement will cause the plurality of arms to move radially away from axis 24 as depicted in FIG. 3 due to the resiliency and original angular orientation of the arms. Such movement of the arms provides access to the interior of the elongated tubular member 16, and the cartridge 4 can therefore be inserted therein until the hub 14 is adjacent the arms. When the cartridge is so positioned, releasing of the section 64 will allow spring 58 to decompress causing the sleeve to move along axis 24 towards end 18 of member 16. Such movement causes a camming action between the sleeve 46 and the arms 20 which urges the arms in a radial direction towards axis 24 and into locking engagement with the hub 14 as depicted in FIG. 4.

In the alternative embodiment of FIGS. 5 and 6, an elongated sleeve 66 is provided including a keyway 68 which extends in the direction of longitudinal axis 24 and outward from outer surface 70 of the sleeve. Body portion 26 of the elongated tubular member 16 includes a corresponding key 72 which extends from outer surface 74 of the body portion. Preferably, the elongated sleeve 66 and elongated tubular member 16 are polypropylene. When the body portion 26 is inserted into the sleeve 66 the key 72 mates with the keyway 68 to facilitate sliding movement of the sleeve relative to the elongated tubular member along axis 24. As in the embodiments of FIGS. 1 to 4A, a camming action of the sleeve relative to the arms moves the arms in a radial direction for engagement with, and the locking in place of, the cartridge. In the embodiment depicted in FIGS. 5 and 6, the keyway 68 includes aperture 76 through a surface 78 thereof, and key 72 is in the form of a resilient locking tab which mates with aperture 76 in a locking position when the plurality of arms 20 have been urged towards axis 24 as depicted in FIG. 6. Preferably, the locking tab 72 and elongated tubular body member 16 are formed by a unitary structure. Depression of the tab allows for movement of the member 16 away from the sleeve 66 so that the resilient arms spring outward relative to the axis 24 to thereby unlock the cartridge 16.

In the embodiments depicted in the drawings each cartridge 4 includes a hub 14 which includes at least one, and preferably a plurality, of recessed areas 80 and the plurality of arms 20 include corresponding arms which mate with such areas when the cartridge has been inserted into the elongated tubular member 16 and the arms have been urged into locking engagement with the hub as discussed herein. For example, in the embodiment of FIGS. 1 and 2, claw-like ends 34 and 36 mate with recessed areas 80 of hub 14. Hub 14 can be formed from any suitable material but is preferably metal such as stainless steel.

All of the embodiments of FIGS. 1 through 6 include means associated with the elongated tubular member 16 for dispensing and aspirating the hypodermic syringe 2 which is formed when cartridge 4 is inserted into and coupled to the member 16. For example, and by way of example only, the embodiment of FIG. 1 is depicted as including a piston rod 82 having a handle 84 at one end to facilitate reciprocating movement of the rod in a known manner. Similarly, cartridge 4 includes a typical plunger 86 therein which is coupled to the piston rod 82 in a known manner such that axial movement of the piston rod causes corresponding axial movement of the plunger to dispense the medicament from the cartridge or receive blood within the cartridge depending upon whether such movement is a dispensing movement or aspirating movement. Piston rod 82 and handle 84 are preferably formed from acetal. In the embodiment of FIG. 1 the piston rod 82 can be coupled to plunger 86 by means of the threaded protuberance 88 and corresponding threaded bore 90. In the embodiments described herein each apparatus can include the section 64 to facilitate operation of the hypodermic syringe when the apparatus is assembled and ready for use.

The preferred materials for forming the embodiments of the present invention have been discussed herein. However, the apparatus of the present invention can be formed from any material useful in the manufacture of hypodermic syringes. If desired various components can be transparent so that the content of the cartridge 4 can be viewed. For example, in FIG. 1 the elongated tubular member 16 can be transparent.

It will be readily apparent that the present invention provides a hypodermic syringe wherein a medical attendant can remove a cartridge assembly including a needle attached thereto from a holder without grasping or otherwise touching such assembly and without such assembly falling out of the holder as a result of the attendant carelessly attempting to grasp the assembly and without the attendant inadvertently dropping the assembly.

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

We claim:

1. Apparatus for use with a cartridge to form a hypodermic syringe, said cartridge including an elongated body having a first end and a second end and having a needle attached to said first end by means of a hub which is attached to one end of said needle, comprising:

an elongated tubular member having one end which includes a plurality of arms extending therefrom and an opposite other end, said arms being moveable in a radial direction relative to a longitudinal axis of said elongated member and being resiliently biased away from said longitudinal axis;

said elongated tubular member being configured such that said cartridge is insertable into said elongated tubular member at said second end of said cartridge until said hub is adjacent said plurality of arms and said needle is extending from said elongated tubular member in the direction of said longitudinal axis;

said elongated member and said plurality of arms being formed by a unitary structure, said elongated tubular member including a body portion, and each arm of said plurality of arms being integrally hinged to said body portion and extending at an angle away from said body portions at a respective hinge;

urging means positioned around said elongated tubular member and being slideable relative to said elongated tubular member in the direction of said longituinal axis, for urging each arm of said plurality of arms towards said longitudinal axis, and into locking engagement with said hub when said cartridge has been inserted into said elongated member, as said means is moved towards said one end and engages said plurality of arms;

said body portion being cylindrical and further wherein said urging means comprises a sleeve having an inner diameter greated than an outer diameter of said body portion to facilitate sliding movement of said sleeve relative to said body portion along said longitudinal axis;

said sleeve being elongated and including a keyway which extends in the direction of said longitudinal axis and outward from an outer surface of said sleeve, and wherein said body portion includes a corresponding key which extends from an outer surface of said body portion and mates with said keyway to facilitate said sliding movement of said sleeve relative to said elongated tubular member along said longitudianl axis;

and means associated with said elongated tubular member for dispensing and aspirating said hypodermic syringe which is formed when said cartridge is inserted into and coupled to said elongated tubular member.

2. The apparatus of claim 1 wherein said keyway includes an aperture through a surface thereof, and further wherein said corresponding key is in the form of a resilient locking tab which mates with said aperture when said arms of said plurality of arms have been urged towards said longitudinal axis.

3. The apparatus of claim 2 wherein said resilient locking tab and said elongated tubular body member are formed by a unitary structure.

4. The apparatus of claim 3 wherein said plurality of arms comprises two pairs of opposing arms.

5. The apparatus of claim 4 wherein said plurality of arms comprises two pairs of opposing claw-like arms.

6. The apparatus of claim 5 wherein each arm of said plurality of arms is circumferentially spaced at about ninety degrees from an adjacent of said arms.

* * * * *